US00PP37797P2

(12) United States Plant Patent
van Dijk

(10) Patent No.: US PP37,797 P2
(45) Date of Patent: Oct. 20, 2026

(54) ***ANTHURIUM* PLANT NAMED 'AN2608457'**

(50) Latin Name: *Anthurium andreanum*
Varietal Denomination: AN2608457

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/559,934

(22) Filed: Mar. 6, 2026

(51) Int. Cl.
*A01H 5/02* (2018.01)
*A01H 6/10* (2018.01)

(52) U.S. Cl.
USPC ..... Plt./369

(58) Field of Classification Search
USPC ..... Plt./263.1, 365, 369
See application file for complete search history.

(56) References Cited

U.S. PATENT DOCUMENTS

PP36,507 P2 * 2/2025 van Dijk ..... Plt./369

* cited by examiner

*Primary Examiner* — Karen M Redden
(74) *Attorney, Agent, or Firm* — C. Anne Whealy

(57) ABSTRACT

A new and distinct cultivar of *Anthurium* plant named 'AN2608457', characterized by its compact, upright to outwardly arching plant habit; freely clumping growth habit; bushy and dense plants; ovate to narrowly cordate dark green-colored leaves; freely flowering habit; inflorescences that are positioned above the foliar plane on sturdy scapes; orbicular to reniform spathes that are bright red in color; and spadices that are white in color with bright yellow-colored apices.

2 Drawing Sheets

Figure 1:
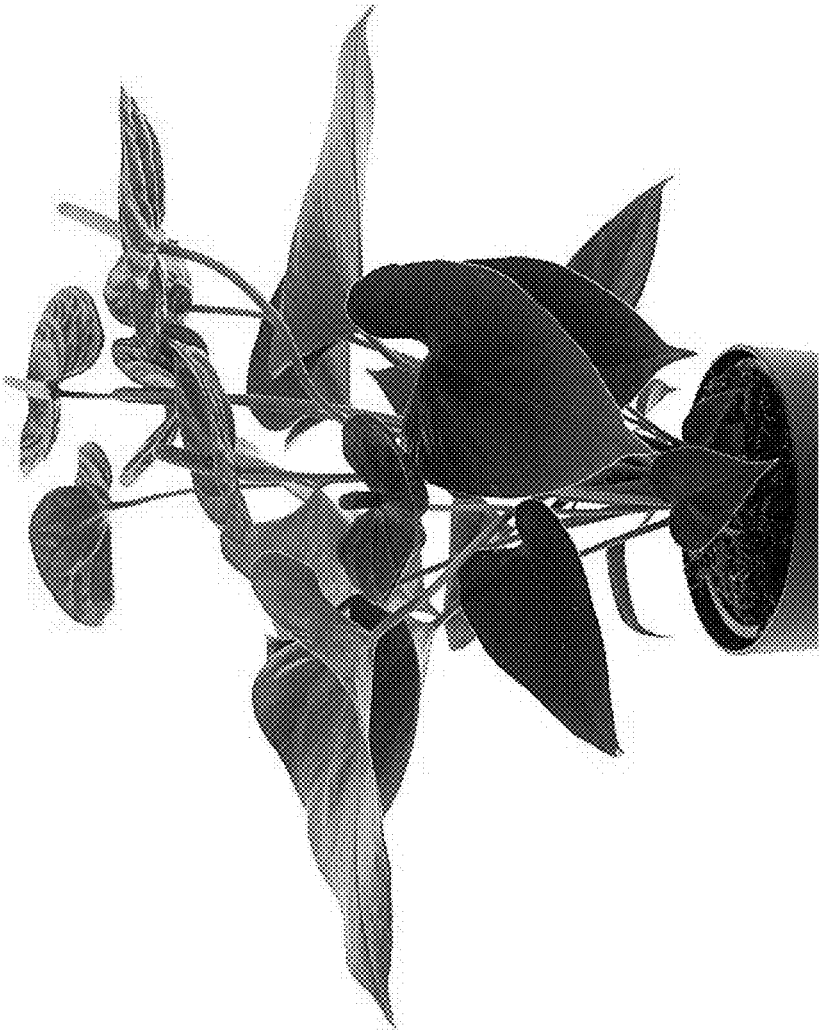

Botanical designation: *Anthurium andreanum.*
Cultivar denomination: 'AN2608457'.

STATEMENT REGARDING PRIOR DISCLOSURES BY APPLICANT

A European Community Plant Breeder's Rights application for the instant plant was filed by the Applicant/Assignee of the instant application, Anthura B.V. of Bleiswijk, The Netherlands on Nov. 20, 2024, application number 2024/2687. Foreign priority is not claimed to this application.

BACKGROUND OF THE INVENTION

The present invention relates to a new and distinct cultivar of *Anthurium* plant, botanically known as *Anthurium andreanum*, commonly referred to as Flamingo Flower and hereinafter referred to by the name 'AN2608457'.

The new *Anthurium* plant is a product of a controlled breeding program conducted by the Inventor in Bleiswijk, The Netherlands. The objective of the breeding program is to create new compact *Anthurium* plants with durable red-colored spathes.

The new *Anthurium* plant originated from a cross-pollination made by the Inventor in May, 2016 in Bleiswijk, The Netherlands of a proprietary breeding selection of *Anthurium andreanum* identified as code number 12-030511-0002, not patented, as the female, or seed, parent with a proprietary breeding selection of *Anthurium andreanum* identified as code number 12-028793-0002, not patented, as the male, or pollen, parent. The new *Anthurium* was discovered and selected by the Inventor as a single flowering plant within the progeny of the stated cross-pollination in a controlled greenhouse environment in Bleiswijk, The Netherlands in February, 2018.

Asexual reproduction of the new *Anthurium* plant by in vitro meristem propagation in a controlled environment in Bleiswijk, The Netherlands since July, 2020 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2608457'. These characteristics in combination distinguish 'AN2608457' as a new and distinct *Anthurium* plant:

1. Compact, upright to outwardly arching plant habit.
2. Freely clumping growth habit; bushy and dense plants.
3. Ovate to narrowly cordate dark green-colored leaves.
4. Freely flowering habit.
5. Inflorescences that are positioned above the foliar plane on sturdy scapes.
6. Orbicular to reniform spathes that are bright red in color.
7. Spadices that are white in color with bright yellow-colored apices.

Plants of the new *Anthurium* differ primarily from plants of the female parent selection in the following characteristics:

1. Plants of the new *Anthurium* have larger spathes than plants of the female parent selection.

2. Spadices of plants of the new *Anthurium* are not as tapering as spadices of plants of the female parent selection.

Plants of the new *Anthurium* differ primarily from plants of the male parent selection in the following characteristics:

1. Spathes of plants of the new *Anthurium* are more concave than and not as flat as spathes of plants of the male parent selection.
2. Spadices of plants of the new *Anthurium* are shorter than spadices of plants of the male parent selection.

Plants of the new *Anthurium* can also be compared to plants of *Anthurium andreanum* 'ANTHGLYNT', disclosed in U.S. Plant Pat. No. 30,967. In side-by-side comparisons, plants of the new *Anthurium* differ primarily from plants of 'ANTHGLYNT' in the following characteristics:

1. Spathes of plants of the new *Anthurium* have broader apices than spathes of plants of 'ANTHGLYNT'.
2. Spadices of plants of the new *Anthurium* are not as tapering as spadices of plants of 'ANTHGLYNT'.

BRIEF DESCRIPTION OF THE PHOTOGRAPHS

The accompanying photographs illustrate the overall appearance of the new *Anthurium*. The photographs show the colors as true as it is reasonably possible to obtain in colored reproductions of this type. Colors in the photographs may differ slightly from the color values cited in the detailed botanical description which accurately describe the colors of the new *Anthurium*.

The photograph on the first sheet (FIG. 1) is a side perspective view of a typical plant of 'AN2608457' grown in a container.

Figure 2:
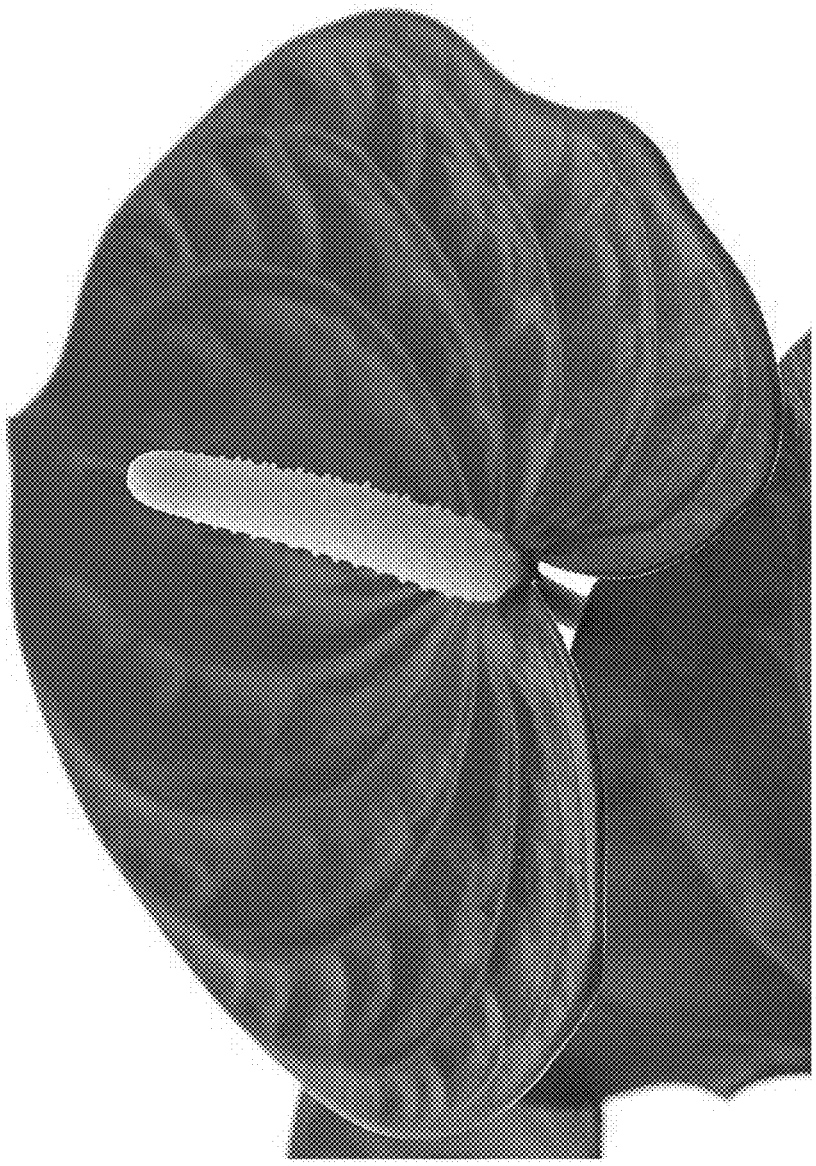

The photograph on the second sheet (FIG. 2) is a close-up view of a typical inflorescence of 'AN2608457'.

DETAILED BOTANICAL DESCRIPTION

The aforementioned photographs and following observations and measurements describe plants grown in 12-cm containers during the early autumn in a glass-covered greenhouse in Bleiswijk, The Netherlands. Plants were grown under conditions and practices which approximate those generally used in commercial *Anthurium* production. During the production of the plants, day and night temperatures ranged from about 19° C. to about 22.5° C. and light levels ranged from about 100 μmol to about 200 μmol. Plants were ten months from planting young rooted plants when the photographs and the detailed description were taken. In the following description, color references are made to The Royal Horticultural Society Colour Chart, 2015 Edition, except where general terms of ordinary dictionary significance are used.

Botanical classification: *Anthurium andreanum* 'AN2608457'.

Parentage:

*Female, or seed, parent*.—Proprietary breeding selection of *Anthurium andreanum* identified as code number 12-030511-0002, not patented.

*Male, or pollen, parent*.—Proprietary breeding selection of *Anthurium andreanum* identified as code number 12-028793-0002, not patented.

Propagation:

*Type*.—By in vitro meristem propagation.

*Time to initiate roots, summer and winter*.—About two weeks at temperatures ranging from about 19° C. to about 22.5° C.

*Time to produce a rooted young plant, summer and winter*.—About six to eight weeks at temperatures ranging from about 19° C. to about 22.5° C.

*Root description*.—Medium in thickness, fibrous; typically creamy white in color; actual color of the roots is dependent on substrate composition, water quality, fertilizer type and formulation, substrate temperature and physiological age of roots.

*Rooting habit*.—Freely branching, medium density.

Plant description:

*Plant shape*.—Compact, upright to outwardly arching plant habit; overall shape, broadly elliptic to globular.

*Growth habit*.—Freely clumping habit imparting a bushy and dense appearance; in a single year of production, about 40 individual plants can be harvested per plant; moderately vigorous growth habit and moderate growth rate.

*Plant height, from soil level to top of leaf plane*.—About 22 cm.

*Plant height, from soil level to top of inflorescences*.—About 30.4 cm.

*Plant diameter or spread*.—About 39.6 cm.

Leaf description:

*Arrangement*.—Alternate; simple.

*Length*.—About 13.2 cm.

*Width*.—About 8.4 cm.

*Shape*.—Ovate to narrowly cordate.

*Apex*.—Bluntly acute with a mucronate tip.

*Base*.—Cordate.

*Margin*.—Entire; slightly and coarsely undulate.

*Texture, upper and lower surfaces*.—Smooth, glabrous; moderately coriaceous.

*Venation pattern*.—Pinnate.

*Color*.—Developing leaves, upper surface: Close to NN137B; narrow marginal edges, close to 152B; mucronate tip, close to 151A; venation, close to 144B. Developing leaves, lower surface: Close to a blend of 146C and 195A; narrow marginal edges, close to 152A; mucronate tip, close to 152C; main vein, close to 144B and secondary venation, close to NN137A. Fully expanded leaves, upper surface: Close to NN137A; narrow marginal edges, close to 144A; mucronate tip, close to 144A; venation, close to a blend of 144A and 146D. Fully expanded leaves, lower surface: Close to 144A; venation, close to 144B.

*Petioles*.—Length: About 12.7 cm. Diameter: Distally, about 3 mm and proximally, about 4 mm. Texture, upper and lower surfaces: Smooth, glabrous. Cplor, upper surface: Close to 144A. Color, lower surface: Close to 144B. Geniculum length: About 2.1 cm. Geniculum diameter: About 4 mm. Geniculum texture, upper and lower surfaces: Smooth, glabrous. Geniculum color, upper surface: Close to 146A. Geniculum color, lower surface: Close to 144A. Wing length: About 1.3 cm. Wing diameter: About 3 mm. Wing texture: Smooth, glabrous. Wing color, upper surface: Close to 146C; towards the margins and apex, close to 144D. Wing color, lower surface: Close to 144A; towards the margins and apex, close to 150D.

Inflorescence description:

*Inflorescence arrangement and flowering habit*.—Spathes with spadices; open inflorescences held above the foliar plane on sturdy scapes; flowering structures arise from leaf axils; freely and continuous flowering year-round in controlled temperature greenhouses in The Netherlands; typically about eight developing and developed inflorescences per plant at one time; inflorescence development commences about 2.5 to 3.5 months after planting rooted young plants.

*Inflorescence longevity*.—On the plant, depending on temperature, spathes maintain good substance for about two months; inflorescences persistent.

*Fragrance*.—None detected.

*Spathes*.—Length: About 9 cm. Width: About 9.2 cm. Shape: Orbicular to reniform; slightly to moderately concave. Apex: Abruptly acute with a mucronate apex; recurved. Base: Cordate. Margin: Entire; revolute. Aspect: About 85° to 95° from the scape axis. Texture, upper and lower surfaces: Smooth, glabrous; moderately coriaceous. Color: When developing, front surface: Close to N45A; narrow marginal edges, close to 46A; mucronate tip, close to 154C. When developing, rear surface: Close to 46B; cordate lobes, close to 47C; narrow marginal edges, close to 46A; mucronate tip, close to 154C. Fully developed, front surface: Close to N45A; narrow marginal edges, close to 46A; mucronate tip, close to 154C; color does not fade with subsequent development. Fully developed, rear surface: Close to 46B; cordate lobes, close to 47C; narrow marginal edges, close to 46A; mucronate tip, close to 154C; color does not fade with subsequent development.

*Spadices*.—Length: About 3.7 cm. Diameter: About 7 mm. Shape: Cylindrical, slightly tapering towards the apex; apex, obtuse; base, obtuse; in cross-section, rounded. Aspect: About 10° to 20° from the scape axis. Color, immature: Close to 155D; towards the apex, close to 13A. Color, mature: Close to 155D; towards the apex, close to 17C. Flowers: Type: Hermaphroditic. Quantity per spadix: About 150.Height: About 1 mm. Diameter: About 2 mm. Shape: Roughly square. Anther color: Close to 153A. Pollen amount: Scarce. Pollen color: Close to 159C. Stigma color: Close to 161A. Ovary color: Close to 158C.

*Scapes*.—Length: About 23 cm. Diameter: About 3 mm. Strength: Sturdy. Aspect: About 12.5° from vertical. Color, upper surface: Close to 144A; distally, closer to N144C. Color, lower surface: Close to 144A; distally, closer to a blend of 144A and 144B.

*Seed and fruit*.—To date, seed and fruit development has not been observed on plants of the new *Anthurium*.

Pathogen & pest resistance: To date, plants of the new *Anthurium* have not been observed to be resistant to pathogens or pests common to *Anthurium* plants.

Temperature tolerance: Plants of the new *Anthurium* have been observed to be tolerant to high temperatures of about 30° C. and to be hardy to USDA Hardiness Zone 10.

It is claimed:

1. A new and distinct *Anthurium* plant named 'AN2608457' as herein illustrated and described.

* * * * *